US011395917B2

(12) United States Patent
Liedler et al.

(10) Patent No.: US 11,395,917 B2
(45) Date of Patent: Jul. 26, 2022

(54) NEUROSTIMULATION USING AC AND/OR DC STIMULATION PULSES

(71) Applicant: Precisis AG, Heidelberg (DE)

(72) Inventors: Angela Liedler, Starnberg (DE); Gregor Remmert, Heidelberg (DE); Dumitru-Ovidiu-Silviu Coman, Bucharest (RO)

(73) Assignee: PRECISIS GmbH, Heidelberg (DE)

(*) Notice: Subject to any disclaimer, the term of this patent is extended or adjusted under 35 U.S.C. 154(b) by 418 days.

(21) Appl. No.: 15/647,905

(22) Filed: Jul. 12, 2017

(65) Prior Publication Data
US 2018/0015286 A1 Jan. 18, 2018

Related U.S. Application Data

(60) Provisional application No. 62/362,614, filed on Jul. 15, 2016.

(51) Int. Cl.
*A61N 1/36* (2006.01)
*A61N 1/05* (2006.01)

(52) U.S. Cl.
CPC ....... *A61N 1/36025* (2013.01); *A61N 1/0534* (2013.01); *A61N 1/0551* (2013.01); *A61N 1/36175* (2013.01)

(58) Field of Classification Search
CPC .................................................. A61N 1/36025
See application file for complete search history.

(56) References Cited

U.S. PATENT DOCUMENTS

| 6,134,461 A * | 10/2000 | Say | A61B 5/14532 |
| | | | 600/345 |
| 6,301,505 B1 | 10/2001 | Money | |
| 10,080,497 B2 * | 9/2018 | Harttig | A61B 5/14865 |
| 2002/0013612 A1 * | 1/2002 | Whitehurst | A61N 1/36096 |
| | | | 607/45 |
| 2007/0255164 A1 * | 11/2007 | Viertio-Oja | A61B 5/6814 |
| | | | 600/558 |
| 2008/0114405 A1 * | 5/2008 | Palmer | A61N 1/37 |
| | | | 607/2 |
| 2010/0070005 A1 * | 3/2010 | Rocke | A61N 1/08 |
| | | | 607/66 |
| 2013/0184794 A1 | 7/2013 | Feldman | |
| 2015/0164354 A1 | 6/2015 | Parker | |
| 2016/0249846 A1 * | 9/2016 | Yoo | A61B 5/0478 |
| | | | 600/544 |

FOREIGN PATENT DOCUMENTS

WO 2015/168735 A1 5/2015

\* cited by examiner

*Primary Examiner* — Rex R Holmes
*Assistant Examiner* — Jennifer L Ghand
(74) *Attorney, Agent, or Firm* — WC&F IP

(57) ABSTRACT

Neurostimulation is performed using electrical AC and/or DC stimulation pulses. Brain and/or spinal cord stimulation of a patient is achieved using an implanted neurostimulation device. Neurostimulation is performed using AC and/or DC stimulation pulses combined with a safe operation in DC mode by discharging build-up loads at the interfaces of the electrodes through short circuiting such stimulation electrodes with a counter electrode, for example a common ground electrode.

19 Claims, 2 Drawing Sheets

NEUROSTIMULATION USING AC AND/OR DC STIMULATION PULSES

CROSS-REFERENCE TO RELATED APPLICATIONS

This application claims priority to U.S. Ser. No. 62/362,614 filed Jul. 15, 2016. The complete contents of the prior application is herein incorporated by reference.

FIELD OF THE INVENTION

The present invention relates to neurostimulation using electrical AC and/or DC stimulation pulses. The invention is particularly related to the area of brain and/or spinal cord stimulation of a patient by means of a neurostimulation device.

Electrical stimulation of neural or nervous tissue, e.g., brain tissue, is a well-established procedure for the treatment of various neurological disorders. It has been successfully applied to treat diseases, such as Morbus Parkinson, epilepsy, migraine, stroke, and many other neurological illnesses or conditions.

BACKGROUND

The established technologies are either highly invasive or require stationary application. The disadvantage of non-invasive treatments of neurological disorders like tDCS or TMS is that they cannot be applied outside of the hospital setting due to the lack of accessible and safe mobile devices for therapeutic purposes. The disadvantage of the established intracranial neurostimulation systems (DBS or RNS) is their invasiveness and the associated risks for the patients.

All commercially available, implantable devices apply AC stimulation because charge build-ups at the electrode interfaces may impair the safe operation of DC devices by inhibiting reliable sensing, causing electrode damage or triggering unwanted chemical side reactions. However, there is evidence that DC stimulation can offer particular advantages in acute and chronic modulation of excitability.

BRIEF SUMMARY OF THE INVENTION

The present invention overcomes all these disadvantages and restrictions by offering neurostimulation using AC and/or DC stimulation pulses combined with a safe operation in DC mode by discharging build-up loads at the interfaces of the electrodes through short circuiting such stimulation electrodes with a counter electrode, for example a common ground electrode or a cathode. The positive effects and advantages of the invention are realized by a neurostimulation device according to claim 1, a method for brain neurostimulation and/or spinal cord neurostimulation according to claim 10, a computer program for controlling a neurostimulation device according to claim 15 and the use of the aforementioned neurostimulation device for brain neurostimulation and/or for spinal cord stimulation according to claim 20. The dependent claims disclose further advantageous embodiments of the invention.

Generally speaking, AC is an abbreviation for Alternating Current and DC is an abbreviation for Direct Current. In the context of the present invention, stimulation pulses are deemed AC stimulation pulses in case of pulse trains with polarity reversal (positive and negative pulses). Stimulation pulses are deemed DC pulses in case of only one-sided stimulation patterns (only positive or only negative) including amplitude swings of predominantly stimulating or inhibiting character or exclusively cathodal or anodal pulse trains. Generally, any pulse trains of stimulation pulses are deemed DC stimulation pulses if they could lead to a significant hyperpolarization effect of nervous and other tissue.

The disclosed device overcomes all these disadvantages and restrictions by offering a minimal invasive implantable device, which is capable of efficiently targeting defined areas of the brain through electrode arrays placed on the cranium, delivering any user-defined combination of AC and/or DC stimulation trains and providing the attending physicians maximum flexibility for adapting and subsequently adjusting stimulation patterns and stimulation modes (AC/DC) to the immediate needs of a patient and to changes over time. It improves the efficiency of neural treatments by providing the option of safe operation in DC mode by discharging built-up loads at the interfaces of the electrodes. This feature enables the application of DC in neurostimulation devices.

It is advantageous for the treatment of several neurological disorders that the invention is capable of adapting not only the stimulation intensity but also the stimulation mode over time, as the focus of a treatment may change by and by from the treatment of primary to that of secondary symptoms associated with a neurological disorder, which in many cases require a different treatment.

Disorders like epilepsy, Morbus Parkinson, dystonia, or Alzheimer's disease for instance are often accompanied by impaired cognitive skills or depression. While the initial treatment of the primary symptoms may require either high frequency AC stimulation or inhibiting respectively stimulating pulses, the subsequent treatment of accompanying secondary symptoms may require different modulation patterns respectively modulation modes.

In the case of epileptic disorders it may for instance be advantageous to start a treatment by delivering inhibiting impulses in order to reduce the seizure frequency, continue with high frequency AC pulses in order to dissolve long-term plasticity, before eventually applying stimulating impulses to treat impaired cognitive skills or depression. The corresponding flexibility required is provided by the present invention and constitutes another advantageous feature of the invention.

Another treatment option could be to deliver a specific modulation pattern as a standard treatment and switch to another stimulation mode in response to specific events. This is another advantageous feature of the invention. An example would be to use the notion of DC substrate modification to reduce epileptic seizure tendency and manage co-morbidity by AC stimulation to terminate or abort specific events as the mainstay of a dual therapy.

It is therefore therapeutically advantageous to have a stimulation device, which covers the entire range of therapeutically possibly relevant AC and DC treatment options. This is another advantageous feature of the invention. However, commercially available, implantable stimulation devices do not provide this functionality.

The present invention discloses a method and a device for the electrical stimulation of brain or other tissue in subjects via implanted electrodes, capable of delivering any user-defined combination of stimulation trains, ranging from (AC) pulse trains with symmetric polarity reversal over stimulation algorithms shifted one-sided towards amplitude swings of predominantly stimulating or inhibiting pulses to exclusively cathodal or anodal (DC) pulses followed by charge balance phases, or AC modulation patterns with overlapping DC stimulation trains.

A programmable control processor of the device of the invention enables the attending physician to remotely program any desired stimulation algorithm. The device comprises an integrated charge balancing system for periodically discharging built-up loads in the double-layers at the electrodes interfaces when operated in DC mode. The integration of such a shorting system allows a safe operation of the device in DC mode.

The disclosed device provides maximum flexibility for the attending physicians to adapt and subsequently adjust the stimulation pattern and stimulation mode to the immediate needs of a patient and their potential changes over time. It improves the efficiency of neural treatments by providing the option of a post-surgical optimization of not only the stimulation pattern but also the stimulation mode.

The invention reduces the risks associated to the implantation of intracranial stimulation electrodes by placing the electrodes in the subgaleal area (above the skull and below the scalp), which is significantly less invasive than the application of depth or cortical electrodes.

The neurostimulation device of the invention can be an implantable neurostimulation device. In particular, it can be a partially and/or temporarily implantable neurostimulation device. The term "partially implantable" means that not all components of the neurostimulation device must be implanted in a patient. E.g, for acute modulation, the electrodes may be implanted in the subgaleal space, but the power unit of neurostimulation device can be kept external for days or weeks. The term "temporarily implantable" means that the neurostimulation device or at least one or more of its components can be implanted for a certain time and are then removed out of the body of the patient.

Generally speaking, there are advantages and risks associated with DC operation. There is evidence that AC treatment is effective. However, there is also evidence from extracranial and in-vitro stimulations that DC stimulation offers particular advantages in acute and chronic modulation of excitability. Studies have shown that anodal (e.g., positively charged) stimulation depolarizes resting membrane potential, resulting in an increase in neuronal excitability and more spontaneous cell firing. In contrast, cathodal (e.g., negatively charged) stimulation hyperpolarizes resting membrane potential, resulting in a concomitant decrease in neuronal excitability and spontaneous cell firing.

A device offering both options, AC and DC, is therefore desirable. It is particularly advantageous in cases where the combination of both AC and DC, in form of alternating or overlapping treatment is even more effective.

However, all currently available implantable electrical brain stimulation devices use AC pulse trains with polarity reversal. In a biphasic current-mode stimulation, it is usually either a leading "cathodic" phase followed by an "anodic" counterpart, or vice versa. The first phase is used for stimulation respectively inhibition, while the second one basically fulfills a charge balance to prevent any tissue or cell damage that can arise from accumulated residual charges. Also damage (corrosion) of the electrodes can be prevented. One-sided stimulation patterns with amplitude swings of predominantly stimulating or inhibiting character or exclusively cathodal or anodal (DC) pulse trains are avoided, because they bear the risk of damaging tissue and/or the electrodes and may even trigger unwanted side reactions at the electrode interfaces. This is due to a charge build-up at the electrode interfaces, which occurs if a constant current flows between electrodes. The constant current causes charge separation at the electrode interfaces. Electrons and ions interact and form an electrical double layer consisting of two parallel regions of charges. The behavior of these interfaces can be described in terms of a capacitor: When capacitors are placed in a circuit with other sources of voltage, they will absorb energy from those sources. A fully discharged capacitor, will initially act as short-circuit when attached to a source of voltage, drawing maximum current as it begins to build a charge. Over time, the capacitor's terminal voltage rises to meet the applied voltage from the source, and the current through the capacitor decreases correspondingly. Once the capacitor has reached the full voltage, it will stop drawing current, and behave essentially as an open-circuit. Disconnected from the power supply the capacitor will store the energy.

AC devices don't face the risks associated with charge accumulation due to electrical double-layers, because the reversing phase basically fulfills a charge balance and prevents any tissue or cell damage and electrode damage that can arise from accumulated residual charges. The disadvantage of AC systems is however that they send alternating stimulating and inhibiting pulses, which limits the therapeutic efficiency in cases where a specific polarity is therapeutically advantageous.

A safe operation of DC neurostimulation devices becomes feasible, if a device comprises an additional component for periodically discharging built-up loads in the double-layers at the electrodes interfaces. The integration of such a charge balancing system allows a safe operation of devices for brain stimulation in a DC mode. Devices for brain stimulation which comprise such a discharging system are capable of delivering almost ideally square wave pulses of the therapeutically desired polarity. Duration, frequency and amplitude of the pulses remain adjustable as in devices without this feature.

Suitable charge balancing systems are the technical solution for a controlled, safe operation of neurostimulation devices in DC mode. All implantable AC operated devices for brain stimulation comprise already control modules, stimulation and communication sub-systems, central processing units, steering logic controllers etc. Any of these devices, be they intracranial in nature with depth or cortical electrodes, extra cranial for stimulation via electrodes between scull and scalp, or in-bone systems stimulating via electrodes within the cranium could be safely operated in a DC mode if a suitable charge balancing system was integrated into the device.

According to an advantageous embodiment of the invention the electrode arrangement comprises at least one center electrode and a plurality of stimulation electrodes surrounding the center electrode. The center electrode can be the aforementioned counter electrode. This has the advantage that the penetration depths of the electrical signal delivered by the stimulation electrode into the tissue can be increased, compared to other electrode configurations. Another advantage is the increased focusing of stimulation.

According to an advantageous embodiment of the invention, the electrode arrangement consists of at least one central disc-type target electrode, forming the counter electrode, and at least two, preferentially four surrounding disc-type secondary electrodes (Pseudo-Laplacian configuration), forming stimulation electrodes, wherein all of the electrodes are fixed on a pad. The current flow through each of the discrete, disc-type secondary electrodes can be individually controlled in order to be maintained equally and constant in each electrode, regardless of variation in load impedance of each electrode.

According to an advantageous embodiment of the invention the device comprises sensors for detecting neurosignals and/or brain activities, wherein the device is configured for detecting neurosignals and/or brain activities via the sensors, for processing the detected signals and for event driven delivery of stimulation pulses to at least one of the stimulation electrodes depending from the detected and/or processed signals. In such way, the device can provide additional health treatment depending on the signals detected by the sensors, thereby creating a closed loop control circuit for neurostimulation.

According to an advantageous embodiment of the invention the charge balancing circuit is configured for individually (and separately) short-circuiting any of the stimulation electrodes with the counter electrode. This has the advantage the short-circuiting can be limited to those electrodes where hyperpolarization effects have reached or exceeded a certain limit.

According to an advantageous embodiment of the invention the charge balancing circuit or a protection circuit controlling the charge balancing circuit has a central control input which is configured for short-circuiting all of the stimulation electrodes with the counter electrode. This has the advantage that all stimulation electrodes can be brought into a safe state, where they are neutralized, e.g. in cases of malfunctions of the control processor or external disturbing influences. This ensures that the current from the stimulation electrodes is diverted safely from the stimulation electrodes to the neutral potential, e.g. to ground, until the device powers off automatically.

According to an advantageous embodiment of the invention the charge balancing circuit comprises Single-Pole Single-Throw (SPST) switches for short circuiting the at least one of the stimulation electrodes with the counter electrode. In such a way, the charge balancing circuit could be realized with small dimensions and low power consumption. The SPST switches can be semiconductor switches, e.g. analog bipolar SPST switches.

According to an advantageous embodiment of the invention the signal generation circuit is configured for delivering bipolar stimulation pulses to at least one of the stimulation electrodes. In such way, the effects of the neurostimulation can be further improved. The charge balancing circuit is designed to work with both polarities, positive and/or negative.

According to an advantageous embodiment of the invention the control processor is configured for delivering a control signal to the charge balancing circuit for controlling short circuiting the at least one of the stimulation electrodes with the counter electrode under least one of the following conditions:
a) Enable short circuiting only if the current that flows through the stimulation electrode is below a certain threshold,
b) Enable short circuiting only if the voltage between the stimulation electrode and the counter electrode is above a certain threshold,
c) Enable short circuiting if one or more time conditions are met.

In such way, it is ensured that any negative effects of the DC stimulation pulses are avoided. The threshold level for the current or the voltage may be changeable, e.g. by programming the neurostimulation device. The same can be done for the time conditions. In particular, the time conditions can be pre-set time intervals.

According to an advantageous embodiment of the invention the device is configured for delivering preventive stimulation pulses at preset algorithms or at fixed time intervals to the at least one stimulation electrode. In such way, a preventive and/or therapeutic treatment of the patient can be realized.

According to an advantageous embodiment of the invention the device comprises a user input element, wherein the device is configured for delivering preset stimulation pulses to the at least one stimulation electrode upon activation of the user input element by a user. The user input element may communicate with a command device, which is not implanted within the patient. In such case, the user may input its commands into the command device, which in turn communicates with the user input element, in order to trigger the treatment with the pre-set stimulation pulses.

An advantageous method for brain neurostimulation and/or spinal cord neurostimulation comprises the following steps:
a) delivering electrical AC and/or DC stimulation pulses via at least one stimulation electrode to the brain or the spinal cord of a patient,
b) short circuiting the at least one stimulation electrode with a counter electrode, if certain charge balancing criteria are fulfilled.

The method can be performed by means of a neurostimulation device, e.g. an neurostimulation device as mentioned hereinbefore.

According to an advantageous embodiment of the aforementioned method the short circuiting of the at least one of the stimulation electrodes with the counter electrode is enabled under least one of the following conditions:
a) Enable short circuiting only if the current that flows through the stimulation electrode is below a certain threshold,
b) Enable short circuiting only if the voltage between the stimulation electrode and the counter electrode is above a certain threshold,
c) Enable short circuiting if one or more time conditions are met.

According to an advantageous embodiment of the aforementioned method neurosignals and/or brain activities are detected and in response to the detected signals or activities event driven stimulation pulses are delivered to the patient through the at least one stimulation electrode.

According to an advantageous embodiment of the aforementioned method preventive stimulation pulses are delivered at preset algorithms or at fixed time intervals to the at least one of stimulation electrode.

According to an advantageous embodiment of the aforementioned method a user activates the delivery of preset stimulation pulses to the at least one of stimulation electrode.

The aforementioned methods and their method steps can be executed by a computer program for controlling a neurostimulation device, in particular a neurostimulation device as defined in claim 1 or its dependent claims. The computer program can be stored in a memory of the neurostimulation device, e.g. in a memory of the control processor.

An advantageous use of a device according to any of claims 1 to 9 is for brain neurostimulation and/or for spinal cord stimulation. In such case, the device can be used for any of the following:
a) for neurostimulation via electrodes, which are positioned in the cranium bone of the patient,
b) for extracranial neurostimulation via extracranial electrodes, which are positioned between scull and scalp of the patient, c) for intracranial neurostimulation via intracranial electrodes, which are positioned inside the cranium of the patient.

DESCRIPTION OF THE INVENTION

The invention is now further explained using an example for a minimal invasive neurostimulation device capable of delivering AC and/or DC stimulation pulses [EASEE].

The disclosed device is fully implantable and delivers stimulation to defined areas of the brain. It can be used for the treatment of various neurological disorders, amongst others refractory epilepsy, where the device prophylactically hinders the occurrence of epileptic seizures by delivering continuous stimulation pulses. A long-term stimulation enables changes in neuronal networks and plasticity to take place, so that a "modulation" effect occurs. Thus the brain will be less susceptible to epileptic seizures and the patient with epilepsy can live a higher quality of life.

Figure 1:
FIG. 1: System overview

The system consists of three fully implantable parts and other accessory parts, as can be seen in FIG. 1:

A specialized electrode array 2, consisting of several electrodes assembled on a pad which is implanted in the subgaleal area (under the scalp but outside the skull). Each of these discrete, disc-type electrodes is individually controlled to create a symmetric electric field underneath the electrodes, which forces the current to travel perpendicular to the electrode surface and thus optimizes the penetration depth.

A power unit 1 containing a battery pack and the other elements including the stimulation/charge balancing control electronics is implanted below the clavicle.

A cable 12 linking the power unit 1 to the electrode array 2 is implanted under the skin.

A device 13 (not implanted) allows trained medical personnel to set the stimulation parameters according to the individual needs of the patient, as well as to test the functionality of the power supply unit (battery life, impedance) and provides access to data recorded by the patient (seizure log) consisting of a programming wand and a physician control center.

A handheld command device 11 (not implanted) enables the patient to record the event of a seizure, check the battery level, trigger the treatment with pre-set stimulation pulses, and turn the system off in case of an emergency.

Figure 2:
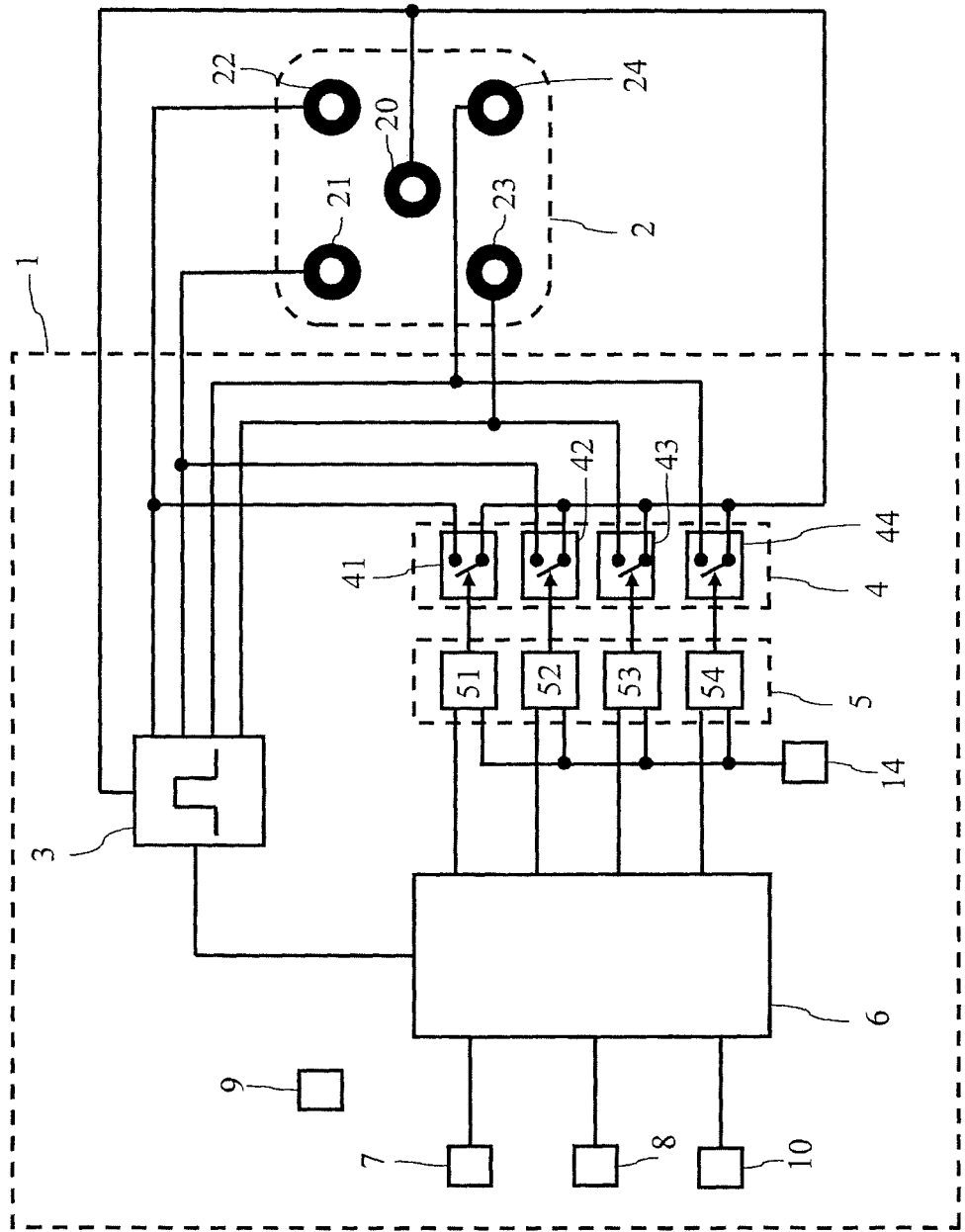
FIG. 2: Graphic presentation of the system with charge balancing system for a device with four secondary electrodes

A more detailed graphic presentation of the system is given in FIG. 2.

FIG. 2 shows the implanted parts of the neurostimulation device in the representation of a block diagram similar to an electric circuit diagram. The power unit 1 comprises a control processor 6, a signal generation circuit 3, a charge balancing circuit 4, a protection circuit 5, sensors 7, 8, a battery pack 9 and a user input element 10. The power unit 1 is connected via the cables 12 to the electrode arrangement 2. As can be seen, the electrode arrangement 2 comprises a counter electrode 20 and four stimulation electrodes 21, 22, 23, 24, which are located around the counter electrode 20 which forms a center electrode. The counter electrode 20 can be a common ground electrode which means that the counter electrode 20 is connected to the common ground of the neurostimulation device respective its power unit 1.

The control processor 6 can be a microcontroller unit (MCU) or any other unit, which can perform control steps via processing of computer programs, e.g. in the form of hardware, firmware or software programs.

The signal generation circuit 3 is able to create and deliver stimulation pulses to the stimulation electrodes 21, 22, 23, 24 upon command from the control processor 6. The signal generation circuit 3 may comprise amplifier components.

The charge balancing circuit 4 comprises four switches 41, 42, 43, 44, one for each stimulation electrode 21, 22, 23, 24. The charge balancing circuit 4 with the four switches may be implemented in the form of an analog bipolar semiconductor device. Through each respective switch 41, 42, 43, 44, any of the stimulation electrodes 21, 22, 23, 24 can be connected and thereby short-circuited to the counter electrode 20.

Each switch 41, 42, 43, 44 comprises a control input, which is connected to a respective output of a protection circuit 5. The protection circuit 5 comprises four logic gates 51, 52, 53, 54, e.g. AND gates. Each output of a logic gate 51, 52, 53, 54 is connected to a control input of a switch 41, 42, 43, 44. For individual control of the switches 41, 42, 43, 44, a first input of each of the logic gates 51, 52, 53, 54 is connected to a dedicated output of the control processor 6. A second input of each of the logic gates 51, 52, 53, 54 are connected in parallel with one single output of a watchdog 14, thus providing a central control input of the protection circuit 5. In normal operating mode, the control processor 6 can control each of the switches 41, 42, 43, 44 separately by means of its dedicated separate outputs connected to the first inputs of the logic gates 51, 52, 53, 54. The watchdog 14 provides an independent safety system which acts in case of a malfunction of the control processor 6 or its software In case of such a malfunction, the watchdog 14 switches all of the switches 41, 42, 43, 44 into the on-state, thereby connecting each of the stimulation electrodes 21, 22, 23, 24 to the counter electrode 20.

The control processor 6 can detect neurosignals and/or brain activities through the sensors 7, 8. The detected neurosignals and/or brain activities can be processed and used for event driven delivery of stimulation pulses to any of the stimulation electrodes 21, 22, 23, 24.

The battery pack 9 supplies the aforementioned elements of the power unit 1 with electrical energy. The battery pack 9 may comprise rechargeable batteries.

The user input element 10 constitutes a wireless communication interface with the external command device 11. By using the command device 11, the user may select certain stimulation programs. The command device 11 sends in such case signals to the user input element 10, which are received by the control processor 6 and implemented in the control of the signal generation circuit 3 and the charge balancing circuit 4.

The signal generation circuit 3 implements bipolar current sources, one for each stimulation electrode 21, 22, 23, 24. In order to achieve a short circuit between the counter electrode 20 and each one of the surrounding stimulation electrodes 21, 22, 23, 24, analog bipolar SPST (Single-Pole Single-Throw) switches are used, one for each stimulation electrode. The charge balancing system further comprises the protection circuit 5 in the form of a hardware logic network, which enables the control processor 6 to control each individual switch 41, 42, 43, 44 and ensures that all stimulation electrodes 21, 22, 23, 24 are short circuited simultaneously when needed. An additional hardware consisting of decoupling capacitors may be placed on all power supplies near each package, in order to avoid coupling noise and spurious signals that appear on the supply voltage pin to the output of the switch. The parameter that evaluates this is the AC Power Supply Rejection Ratio (ACPSRR).

Each switch 41, 42, 43, 44 may short-circuit positive and negative voltage due to the bipolar nature of the therapy current. All switches are placed in one package for optimal size ratio. The protection circuit 5 comprises AND logic gates, one for each electrode, two in each package. It ensures that all stimulation electrodes 21, 22, 23, 24 are short circuited at once, if for instance a malfunction occurs and the device delivers out of control currents. In such a case, all stimulation electrodes 21, 22, 23, 24 are connected to the neutral reference potential i.e. to the common referenced counter electrode 20, which is connected to the housing of the device. This ensures that the current is diverted safely from the stimulation electrodes 21, 22, 23, 24 to the ground until the device powers off automatically.

The invention claimed is:

1. A method for brain neurostimulation and/or spinal cord neurostimulation, comprising:
a) with at least an electrode arrangement, delivering at least DC electrical stimulation pulses via at least two implanted stimulation electrodes of the electrode arrangement to the brain or the spinal cord of a patient, wherein the electrode arrangement comprises at least three electrodes configured for implantation, including the at least two implanted stimulation electrodes and at least one implanted counter electrode,
b) with at least a signal generation circuit connected to the electrode arrangement, generating and delivering the at least DC electrical stimulation pulses to the at least two implanted stimulation electrodes,
c) with at least a charge balancing circuit for compensation of hyperpolarization effects, short circuiting the at least two implanted stimulation electrodes directly with the implanted counter electrode depending from a control signal,
d) with at least one control processor, delivering the control signal to the charge balancing circuit for short circuiting the at least two implanted stimulation electrodes directly with the implanted counter electrode, and
e) with a watch dog, short circuiting all of the implanted stimulation electrodes with the implanted counter electrode at once independently of the at least one control processor.

2. The method according to claim 1, wherein the short circuiting of at least one of the at least two implanted stimulation electrodes with the implanted counter electrode is enabled under least one of the following conditions:
a) enable short circuiting only if the current that flows through the at least one of the at least two implanted stimulation electrodes is below a certain threshold,
b) enable short circuiting only if the voltage between the at least one of the at least two implanted stimulation electrodes and the implanted counter electrode is above a certain threshold,
c) enable short circuiting if one or more time conditions are met.

3. The method according to claim 1, further comprising detecting neurosignals and/or brain activities and in response to the detected neurosignals and/or brain activities delivering event driven stimulation pulses to the patient through the at least two implanted stimulation electrodes.

4. The method according to claim 1, wherein preventive stimulation pulses are delivered at preset algorithms or at fixed time intervals to the at least two implanted stimulation electrodes.

5. The method according to claim 1, further comprising activating by a user delivery of preset stimulation pulses to the at least two implanted stimulation electrodes.

6. A computer program for controlling a neurostimulation device, for performing brain stimulation and/or spinal cord stimulation by delivering at least DC electrical stimulation pulses, the computer program causing the following steps when the computer program is run on at least one control processor of the neurostimulation device:
a) with at least an electrode arrangement, delivering at least DC electrical stimulation pulses via at least two implanted stimulation electrodes of the electrode arrangement to the brain or the spinal cord of a patient, wherein the electrode arrangement comprises at least three electrodes configured for implantation, including the at least two implanted stimulation electrodes and at least one implanted counter electrode,
b) with at least a signal generation circuit connected to the electrode arrangement, generating and delivering the at least DC electrical stimulation pulses to the at least two implanted stimulation electrodes,
c) with at least a charge balancing circuit for compensation of hyperpolarization effects, short circuiting the at least two implanted stimulation electrodes directly with the implanted counter electrode depending from a control signal,
d) with the least one control processor, delivering the control signal to the charge balancing circuit for short circuiting the at least two implanted stimulation electrodes directly with the implanted counter electrode, and
e) with a watch dog, short circuiting all of the implanted stimulation electrodes with the implanted counter electrode at once independently of the at least one control processor.

7. The computer program according to claim 6, wherein the short circuiting of at least one of the at least two implanted stimulation electrodes with the implanted counter electrode is enabled under least one of the following conditions:
a) enable short circuiting only if the current that flows through the at least one of the at least two implanted stimulation electrodes is below a certain threshold,
b) enable short circuiting only if the voltage between the at least one of the at least two implanted stimulation electrodes and the implanted counter electrode is above a certain threshold,
c) enable short circuiting if one or more time conditions are met.

8. The computer program according to claim 6, wherein the computer program further causes detecting neurosignals and/or brain activities and in response to the detected neurosignals and/or brain activities delivering event driven stimulation pulses to the patient through the at least two implanted stimulation electrodes.

9. The computer program according to claim 6, wherein preventive stimulation pulses are delivered at preset algorithms or at fixed time intervals to the at least two implanted stimulation electrodes.

10. The computer program according to claim 6, wherein the computer program further causes receiving activation from a user for the delivery of preset stimulation pulses to the at least two implanted stimulation electrodes.

11. A neurostimulation device, for performing brain stimulation and/or spinal cord stimulation by delivering at least DC electrical stimulation pulses, comprising:
a) at least an electrode arrangement for delivering the at least DC electrical stimulation pulses to the brain or the spinal cord of a patient, wherein the electrode arrangement comprises at least three electrodes configured for implantation, at least two of the electrodes being stimulation electrodes and at least one of the electrodes being a counter electrode,
b) at least a signal generation circuit connected to the electrode arrangement, wherein the signal generation circuit is configured for generating and delivering the at least DC electrical stimulation pulses to the at least two stimulation electrodes,
c) at least a charge balancing circuit for compensation of hyperpolarization effects, which is configured for short circuiting the at least two stimulation electrodes directly with the counter electrode after the at least two stimulation electrodes and counter electrode are implanted, depending from a control signal,
d) at least one control processor, which is configured for delivering the control signal to the charge balancing circuit for short circuiting the at least two stimulation electrodes directly with the counter electrode, and
e) a watch dog arranged for short-circuiting all of the stimulation electrodes with the counter electrode at once independently of the at least one control processor.

12. The neurostimulation device according to claim 11, wherein the electrode arrangement comprises a plurality of counter electrodes.

13. The neurostimulation device according to claim 11, wherein the neurostimulation device comprises sensors for detecting neurosignals and/or brain activities,
wherein the neurostimulation device is configured for detecting neurosignals and/or brain activities via the sensors, for processing the detected neurosignals and/or brain activities, and for event driven delivery of stimulation pulses to at least one of the at least two stimulation electrodes depending from the detected and/or processed neurosignals and/or brain activities.

14. The neurostimulation device according to claim 11, wherein the charge balancing circuit comprises one or more Single-Pole Single-Throw (SPST) switches for short circuiting at least one of the at least two stimulation electrodes with the counter electrode, wherein the at least one of the at least two stimulation electrodes is directly shortable with the counter electrode using a single SPST switch of the SPST switches.

15. The neurostimulation device according to claim 11, wherein the signal generation circuit is configured for delivering bipolar stimulation pulses to at least one of the at least two stimulation electrodes.

16. The neurostimulation device according to claim 11, wherein the at least one control processor is configured for delivering a control signal to the charge balancing circuit for controlling short circuiting of at least one of the at least two stimulation electrodes with the counter electrode under at least one of the following conditions:
a) enable short circuiting only if the current that flows through the at least one of the at least two stimulation electrodes is below a certain threshold,
b) enable short circuiting only if the voltage between the at least one of the at least two stimulation electrodes and the counter electrode is above a certain threshold,
c) enable short circuiting if one or more time conditions are met.

17. The neurostimulation device according to claim 11, wherein the neurostimulation device is configured for delivering preventive stimulation pulses at preset algorithms or at fixed time intervals to the at least two stimulation electrodes.

18. The neurostimulation device according to claim 11, wherein the neurostimulation device comprises a user input element, wherein the neurostimulation device is configured for delivering preset stimulation pulses to the at least two stimulation electrodes upon activation of the user input element by a user.

19. The neurostimulation device according to claim 11, wherein the short circuiting is potential free.

* * * * *